(12) United States Patent
Chu

(10) Patent No.: US 10,828,053 B2
(45) Date of Patent: Nov. 10, 2020

(54) MEDICAL DEVICE HANDLES AND RELATED METHODS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MA (US)

(*) Notice: Subject to any disclaimer, the term of this patent is extended or adjusted under 35 U.S.C. 154(b) by 377 days.

(21) Appl. No.: 15/803,429

(22) Filed: Nov. 3, 2017

(65) Prior Publication Data

US 2018/0125516 A1 May 10, 2018

Related U.S. Application Data

(60) Provisional application No. 62/417,603, filed on Nov. 4, 2016.

(51) Int. Cl.
| | |
|---|---|
| *A61B 17/28* | (2006.01) |
| *A61B 17/70* | (2006.01) |
| *A61B 17/42* | (2006.01) |
| *A61B 1/00* | (2006.01) |
| *A61B 17/221* | (2006.01) |
| *A61B 17/3211* | (2006.01) |
| *A61B 17/00* | (2006.01) |
| *A61B 17/02* | (2006.01) |

(52) U.S. Cl.
CPC ...... *A61B 17/2841* (2013.01); *A61B 1/00066* (2013.01); *A61B 1/00133* (2013.01); *A61B 17/221* (2013.01); *A61B 17/4241* (2013.01); *A61B 17/7065* (2013.01); *A61B 1/00039* (2013.01); *A61B 17/0206* (2013.01); *A61B 2017/0034* (2013.01); *A61B 2017/00336* (2013.01); *A61B 2017/00424* (2013.01); *A61B 2017/2212* (2013.01); *A61B 2017/32113* (2013.01)

(58) Field of Classification Search
CPC ............ A61B 17/0206; A61B 17/2841; A61B 17/4241; A61B 17/7065; A61B 17/221; A61B 1/00039; A61B 1/00066; A61B 1/00133; A61B 2017/0336; A61B 2017/0034; A61B 2017/00424; A61B 2017/2212; A61B 2017/32113
See application file for complete search history.

(56) References Cited

U.S. PATENT DOCUMENTS

| | | | |
|---|---|---|---|
| 9,220,526 B2 | 12/2015 | Conlon | |
| 2005/0272975 A1* | 12/2005 | McWeeney | A61M 25/0068 600/113 |

* cited by examiner

*Primary Examiner* — Brandy S Lee
(74) *Attorney, Agent, or Firm* — Bookoff McAndrews, PLLC

(57) ABSTRACT

A medical insertion device may include a handle including a proximal portion, an intermediate portion, and a distal portion. A delivery shaft may be coupled to a distal most end of the distal portion of the handle. The handle may further include a deflection lever, and a hub for introduction of a medical device, the hub and the deflection lever both being located in the proximal portion of the handle.

16 Claims, 5 Drawing Sheets

MEDICAL DEVICE HANDLES AND RELATED METHODS

CROSS-REFERENCE TO RELATED APPLICATIONS

This application claims the benefit of priority to U.S. Provisional Application No. 62/417,603, filed Nov. 4, 2016, which is incorporated by reference herein in its entirety.

TECHNICAL FIELD

Various aspects of the present disclosure relate generally to medical device handles and related methods. More specifically, the present disclosure relates to medical device handles for selectively extending and retracting an end effector of an elongate device.

BACKGROUND

Medical devices, such as lasers, needles, infusion tubes, sensors, expandable baskets, retrieval devices, and the like may include an elongate member or shaft, and may be arranged for delivery through a working channel of an insertion device (e.g., an endoscope such as, for example, a ureteroscope, a hysteroscope, a bronchoscope, a cystoscope, and similar devices). The elongate member of such medical devices may be selectively extended and retracted relative to the working channel of the insertion device or the medical device's sheath to deploy or retract the elongate member to perform one or more therapies, treatments, or diagnostic evaluations on a subject. For example, the medical device may include an end effector such as an expandable basket at a distal end of the elongate member arranged for delivery through a working channel of a ureteroscope. However, positioning the insertion device and manipulating the elongate member and end effector may require multiple medical professionals, necessitating complex coordination to accurately position and deploy the elements. As such, multiple medical professionals may be required to spend time tediously positioning and maneuvering the insertion device and the elongate member. Such efforts may increase the length, cost, and/or complexity of the medical procedure.

The devices and methods of the current disclosure may rectify some of the deficiencies described above or address other aspects of the prior art.

SUMMARY

Examples of the present disclosure relate to, among other things, medical devices. Each of the examples disclosed herein may include one or more of the features described in connection with any of the other disclosed examples.

In one example, a medical insertion device may include a handle including a proximal portion, an intermediate portion, and a distal portion. A distal shaft may be coupled to a distal most end of the distal portion of the handle. The handle may further include a deflection lever, and a hub for introduction of a medical device, the hub and the deflection lever both being located in the proximal portion of the handle.

The medical device may further include one or more of the following features. The deflection lever may be positioned on a rounded proximal corner of the handle of the insertion device. The deflection lever may deflect a distal end of the delivery shaft through rotational movement of the deflection lever around the round proximal corner. The hub may be located on an opposite side of the proximal portion of the handle from the deflection lever. When the deflection lever is at a distal most position, the deflection lever is substantially parallel to the hub. When the deflection lever is at a proximal most position, the deflection lever may form an acute angle relative to the longitudinal axis of the hub. The hub may be distal to the deflection lever in the proximal portion of the handle.

The hub may extend normal to the longitudinal axis of the handle. The proximal portion of the handle may be wider than the intermediate portion of the handle. The hub may be located in a recessed portion of the proximal portion of the handle. The handle may further include a medical device clip extending on a same side of the handle as the deflection lever.

The medical insertion device may further include a medical device having an end effector at a distal end of an elongate member, and a knob at a proximal end of the elongate member operable to extend and/or rotate the end effector. The medical device may be coupled to the handle and through the delivery shaft via the hub. Axial action on the knob may cause a plunger to push the elongate member distally, and rotational action on the knob may cause the plunger to rotate the elongate member. The medical device may be coupled to the hub via a cap of the medical device, and the plunger may extend from the handle normal to the interface of the cap and the hub. Axial movement of the plunger may be biased by a spring surrounded by a spring housing. The spring housing may be at least partially surrounded by at least one of a seal or a flush indicator.

In another example, a medical system may include a medical insertion device including a handle having a proximal portion, an intermediate portion, and a distal portion, and a delivery shaft, where the handle has a deflection lever in the proximal portion of the handle. The medical system may also include a medical device having an end effector at a distal end of an elongate member and a knob operable to extend and/or rotate the end effector, and the medical device may be coupled to the insertion device through a hub to a distal end of the delivery shaft, where a portion of the medical device includes at least a portion located within the proximal portion of the handle when coupled to the handle.

The medical system may further include that the medical device is coupled to the hub via a cap. The knob may be coupled to a plunger such that action on the knob pushes axially and/or rotates the plunger to extend and/or rotate the elongate member out of a distal opening in the distal end of the delivery shaft. The axial movement of the plunger may be biased by a spring. The hub and the deflection lever may be on opposite sides of the proximal portion of the handle, and the plunger may extend normal to the longitudinal axis of the handle. The hub and the deflection lever may be on the same side of the proximal portion of the handle, and the knob may extend parallel to the longitudinal axis of the handle.

In another example, a method of treatment with a medical system may include a medical insertion device and a medical device, where the insertion device includes a delivery shaft and a handle having a deflection lever and a hub, and where the medical device is coupled to the insertion device via the hub and includes an end effector at a distal end of an elongate member and a knob operable to extend and/or rotate the end effector. The method may include holding the handle in a user's hand, actuating the deflection lever with a thumb of the user's hand to deflect a distal end of the delivery shaft, and actuating the knob with an index finger of the user's hand to extend and/or rotate the end effector from a distal opening in the distal end of the delivery shaft. The method may further include gripping a proximal end of the delivery shaft with the user's other hand to adjust a position of the delivery shaft.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises, has, or includes a list of elements does not include only those elements, but may include other elements not expressly listed or inherent to such a process, method, article, or apparatus. Additionally, the term "exemplary" is used herein in the sense of "example," rather than "ideal."

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical device systems for deployment of a medical device therethrough. The medical device may be delivered through any appropriate insertion device, and may include any one or more end effectors such as, e.g., a retrieval basket.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical system. When used herein, "proximal" refers to a position relatively closer to the exterior of the body or closer to an operator using the medical system. In contrast, "distal" refers to a position relatively further away from the operator using the system, or closer to the interior of the body.

Figure 1:
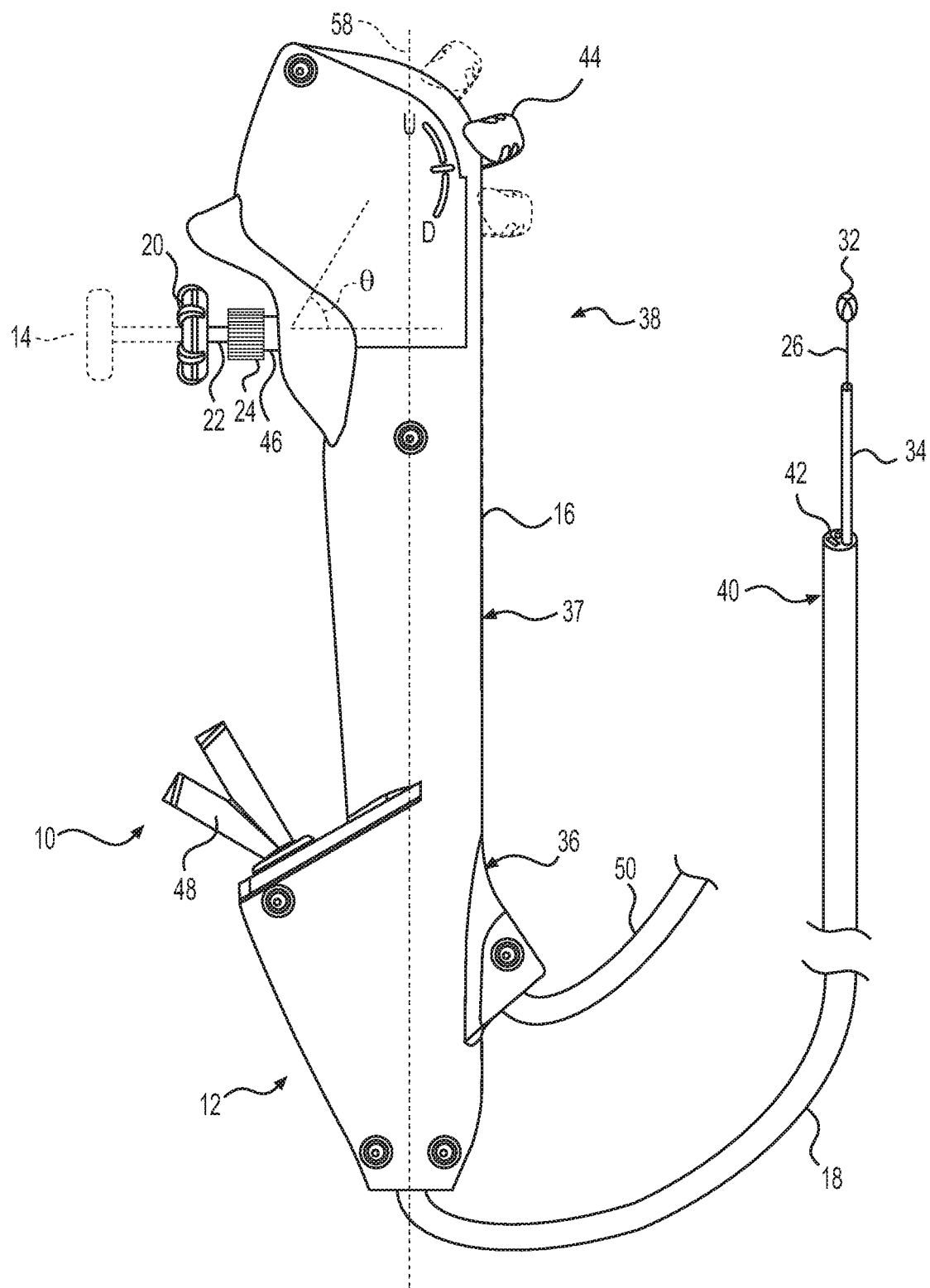
FIG. 1 illustrates an exemplary medical system having an insertion device and a retrieval device.

FIG. 1 illustrates a medical system 10, including an insertion device 12 and a medical device 14. Insertion device 12 may include a handle 16 and a delivery shaft 18. Medical device 14 may include a knob 20, a plunger 22, a cap 24, and an elongate member 26. Elongate member 26 may terminate distally in an end effector 32 and may be at least partially surrounded by a sheath 34.

Medical device 14 will be described as a retrieval basket device, however, it is understood that medical device 14 may be any type of medical device used in conjunction with insertion device 12 to deliver medical therapy to a target site inside a subject. For example, medical device 14 may alternatively be a laser fiber, an irrigation and/or aspiration tube, a snare, forceps, and/or a needle.

Insertion device 12 may be a ureteroscope (e.g., LithoVue™ Single-Use Digital Flexible Ureteroscope by Boston Scientific Corp.), an endoscope, a hysteroscope, a bronchoscope, a cystoscope, or any other similar device. Handle 16 of insertion device 12 includes a distal portion 36, an intermediate portion 37, and a proximal portion 38. As shown in FIG. 1, the curvature of a recessed portion on one side of the handle 16 may define the proximal portion 38. The intermediate portion 37 may be the relatively constant thickness portion of the handle 16, and the distal portion 36 may be defined by port 48. Delivery shaft 18 extends from the distal end of the distal portion 36 of handle 16. A distal end 40 of delivery shaft 18 may have at least one distal opening 42 and may be steered through movement of deflection lever 44 at the proximal portion 38 of handle 16.

Proximal portion 38 of handle 16 may also include a hub 46 in the recessed portion on one side of the proximal portion 38. Hub 46 may extend normal to a longitudinal axis 58 of insertion device 12. Proximal portion 38 of handle 16 may be expanded or have a shape wider than intermediate portion 37 to provide a form-fitting shape to be ergonomically held by a user's hand. Deflection lever 44 may be on a side of handle 16 opposite to hub 46. In one instance, deflection lever 44 is positioned on a rounded corner portion of the proximal portion 38. Then, when held by a user, a user's thumb may manipulate deflection lever 44, and user's index finger on the same hand may manipulate knob 20 with medical device 14 coupled to handle 16 via hub 46. Moreover, medical device 14 coupled via hub may be subjected a force to cause axial or linear movement, while deflection lever 44 may be subjected to force, either proximally or distally, to cause rotational movement along the rounded corner portion of the proximal portion 38 of handle 16. In its most distal position, deflection lever 44 may be substantially parallel to medical device 14. In its most proximal position, deflection lever may form an acute angle θ relative to hub 46 and medical device 14.

Hub 46 may be threaded such that cap 24 of medical device 14 may be secured to hub 46. Alternatively, cap 24 may be a male luer, and hub 46 may be a female luer. Hub 46 may internally connect to a lumen extending through handle 16 and the delivery shaft 18 to distal opening 42 in distal end 40 of delivery shaft 18 such that elongate member 26 may be inserted through the delivery shaft 18 of insertion device 12. The lumen connecting hub 46 may extending straight from hub 46 with a constant width perpendicular to an opposing face of the opposite side of the proximal portion 38, before turning distally to connect to distal opening 42.

Figure 2:
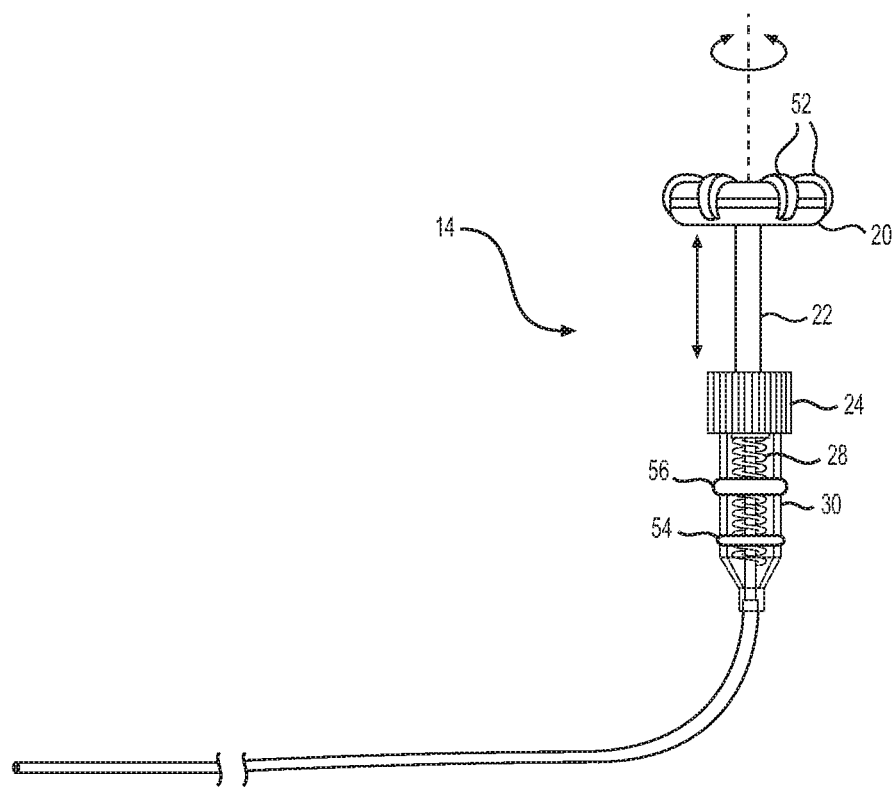
FIG. 2 illustrates a perspective view of the retrieval device of FIG. 1.

Handle 16 may include a port 48, which may be a Y-connector as shown in FIGS. 1 and 2. Port 48 may also internally connect one or more lumens extending through handle 16 and delivery shaft 18 to one or more distal openings 42 in the distal end 40 of the delivery shaft 18 such that various other medical devices may be inserted through the delivery shaft 18 of the insertion device 12. In one aspect, a lumen from port 48 may provide access to the lumen connecting hub 46, and in another aspect the lumens from port 48 and hub 46 may be separate. Though not shown, insertion device 12 may include an integral camera at the distal end that is connected to processing software and a display via a communication and power conduit 50.

As shown in FIG. 2, medical device 14 may include knob 20 with a plurality of protrusions 52 radially positioned around the knob 20. Plunger 22 may be coupled to knob 20 and connected to elongate member 26. In one aspect, both plunger 22 and elongate member 26 may have a circular cross-section. Cap 24 may have an axial lumen such that, when pressure is applied to knob 20, plunger 22 may slide through cap 24 and push elongate member 26 distally. Plunger 22 may be positioned perpendicularly to cap 24, and thus also perpendicularly to both the interface of cap 24 with hub 46 and handle 16. Knob 20 may also be rotatable to transmit the rotation through plunger 22 to elongate member 26. Cap 24 may also include a seal (not shown) around plunger 22. Cap 24 may also be connected to spring housing 30. Cap 24 may be internally connected to spring housing 30, and cap 24 may have internally facing threading on a portion of cap 24 that is radially external to the connection to spring housing 30. Spring housing 30 surrounds spring 28, which provides a biasing force against the distal end of plunger 22. Sheath 34 may be fixedly coupled to an interior portion of cap 24 or to a distal end of spring housing 30.

Medical device 14 may be introduced into insertion device 12 through hub 46, such that knob 20 and plunger 22 are on an opposite side of handle 16 from deflection lever 44. Once elongate member 26 is fully introduced to hub 46, cap 24 may be threaded onto hub 46, enclosing spring housing 30 and spring 28 within insertion device 12.

As shown in FIGS. 1 and 2, elongate member 26 and sheath 34 may have a length such that with cap 24 fully mounted and coupled on hub 46 and without action on plunger 22, elongate member 26 and sheath 34 are flush with or extend slightly distal to the distal end 40 of delivery shaft 18. Then, depression of plunger 22 via knob 20 pushes elongate member 26 distally out of sheath 34 (FIG. 1). If elongate member 26 has a self-expanding basket as end effector 32, the expandable basket expands as it extends out from the sheath 34 and delivery shaft 18. A user may rotate end effector 32 by rotating knob 20 to aid in expanding the expandable basket, in capturing a stone or material, or in repositioning or releasing a captured stone or material. Spring 28 serves to provide a biasing force to return knob 20 and plunger 22 once the force is removed, returning the elongate member 26 to its initial position within the sheath 34. The aforementioned steps may be repeated if the retrieval was unsuccessful. If successful, medical device 14 may be removed from insertion device 12 with the retrieved material captured and enclosed by the elongate member 26 and sheath 34, or medical device 14 may be removed from a subject with removal of the insertion device 12.

As shown in FIG. 2, medical device 14 may also include a seal 54 radially surrounding spring housing 30 to form a seal interior to handle 16. Seal 54 may be an O-ring, wiper seal, or the like, and may be selectively positioned along the length of spring housing 30.

FIG. 2 also illustrates that, in one example, medical device 14 may include a sheath flush indicator marker 56. Here, elongate member 26 and sheath 34 may have a length such that elongate member 26 and sheath 34 extend distally from distal opening 42 a desired distance when cap 24 is coupled to hub 46. Sheath flush indicator marker 56, like seal 54, may be selectively positioned along length of spring housing 30. Sheath flush indicator marker 56 may have a thickness that allows spring housing 30 to be stationary and stable within the inner diameter of hub 46. Sheath flush indicator marker 56 may also be at least partially compressible such that spring housing 30 with both seal 54 and sheath flush indicator 56 may be fully inserted into hub 46, and cap 24 may be securely coupled to hub 46. Sheath flush indicator marker 56 allows a user to mark the insertion position of medical device 14 into hub 46 of insertion device 12 at which sheath 34 and non-extended elongate member 26 are flush with distal opening 42 of delivery shaft 18.

In one aspect, medical device 14 may be inserted such that sheath flush indicator marker 56 is flush with the proximal-most end of hub 46 to retain distal ends of elongate member 26 and sheath 34 within delivery shaft 18 during insertion of insertion device 12 into a subject. Once insertion device 12 is positioned, elongate member 26 and sheath 34 may be extended beyond the distal opening 42 of delivery shaft 18 by pushing medical device 14 distally to couple cap 24 to hub 46, as shown in FIG. 1. Cap 24 may be partially threaded to hub 46 such that elongate member 26 and sheath 34 slightly extend beyond the distal opening 42, or cap 24 may be fully threaded to hub 46 such that elongate member 26 and sheath 34 extend distally from the distal opening 42 the desired distance. Elongate member 26 and sheath 34 may be retracted within delivery shaft 18 by uncoupling cap 24 from hub 46 and retracting medical device 14 until sheath flush indicator marker 56 is flush with or above hub 46.

Figure 3:
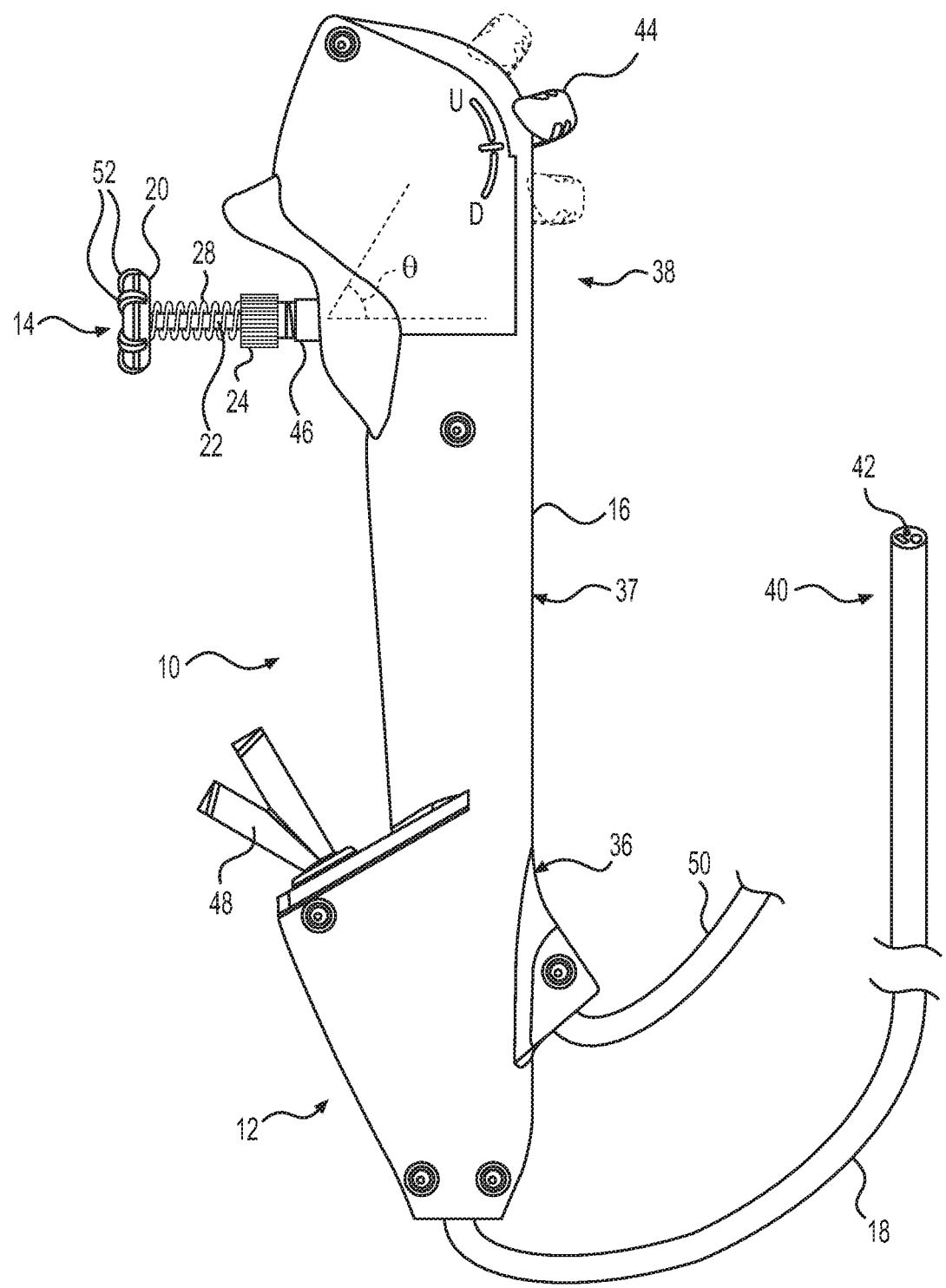
FIG. 3 illustrates an additional exemplary medical device, according to aspects of this disclosure.

In another example, as shown in FIG. 3, elongate member 26 may be employed without a surrounding sheath, and spring 28 may surround plunger 22. Here, elongate member 26 may have a length such that with cap 24 fully mounted on hub 46 and without action on plunger 22, elongate member 26 is flush with or slightly recessed in the distal end 40 of delivery shaft 18 of insertion device 12, as shown in FIG. 3. Then, action on plunger 22 through knob 20 pushes elongate member 26 distally out of delivery shaft 18, similar to as shown in FIG. 1. If elongate member 26 has a self-expanding basket as end effector 32, the expandable basket expands as it extends out from the delivery shaft 18. A user may also rotate the extended elongate member 26 and its end effector 32 by rotating knob 20. For example, a user may rotate end effector 32 to aid in expanding the expandable basket, in capturing a stone or material, or in repositioning or releasing a captured stone or material. Spring 28 serves to provide a biasing force to return knob 20 and plunger 22 once the force is removed, returning the elongate member 26 and end effector 32 to its initial position within the delivery shaft 18. The aforementioned steps may be repeated if the retrieval was unsuccessful. If successful, medical device 14 may be removed from insertion device 12 with the retrieved material captured and enclosed by the elongate member 26, or medical device 14 may be removed from a subject with removal of the insertion device 12.

The foregoing examples allow a user to extend and rotate elongate member 26 with end effector 32 from distal opening 42 in distal end 40 of delivery shaft 18 with the user's index finger acting on knob 20 and plunger 22. Concurrently or sequentially, the user may deflect the distal end 40 of delivery shaft 18 with the user's thumb acting on deflection lever 44. If the two maneuvers are performed concurrently, end effector 32 may be held in an extended position with a user's index finger while the user controls and/or deflects the distal end 40 of delivery shaft 18 with the his or her thumb. The medical device 10 of this disclosure further allows the user to use his or her other hand to control and/or adjust the distal insertion or proximal retraction of delivery shaft 18 of insertion device 12 by, for example, gripping the proximal end of delivery shaft 18 with his or her other hand.

Figure 4:
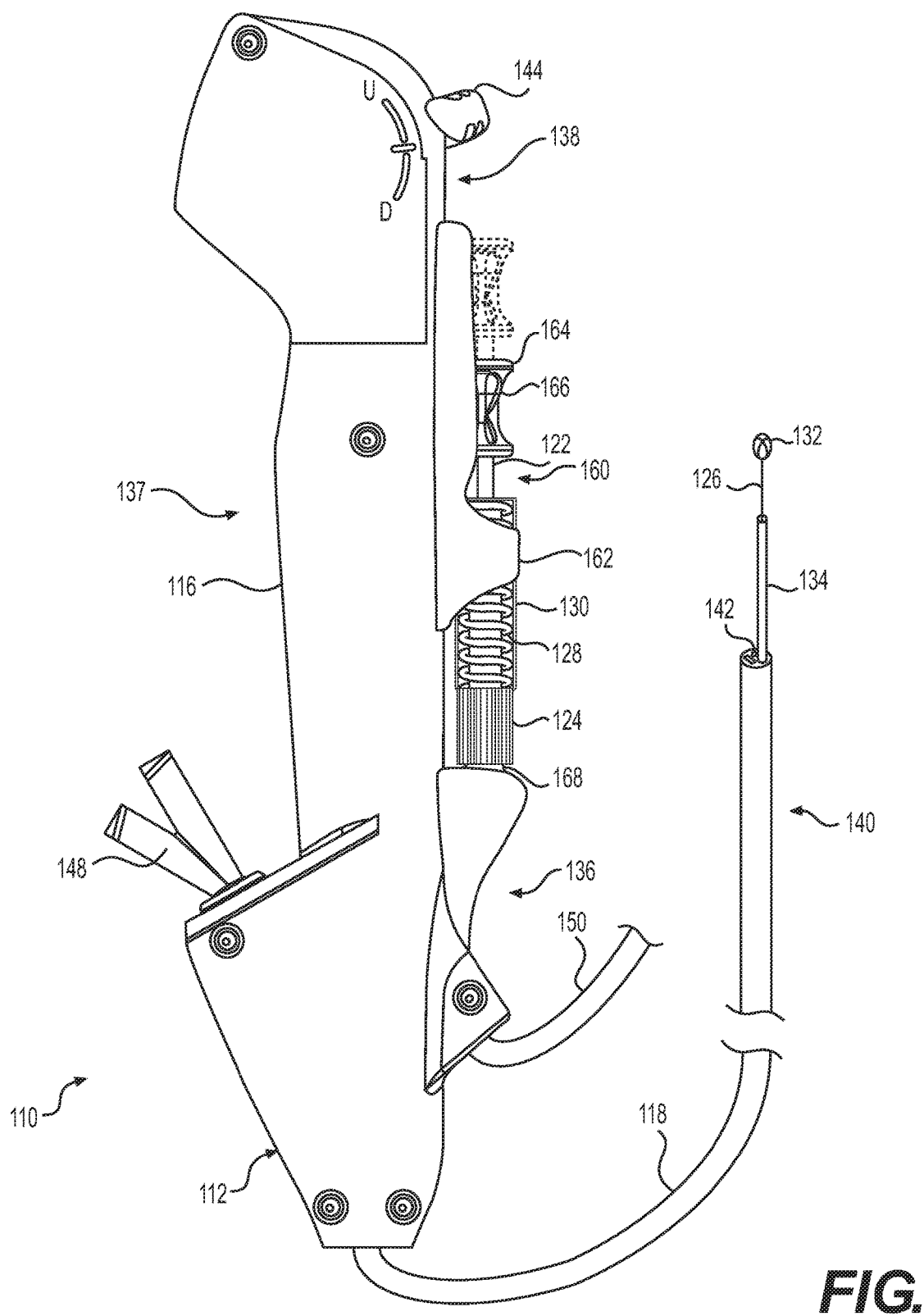
FIG. 4 illustrates an additional exemplary medical device, according to aspects of this disclosure.

As shown in FIG. 4, which is an alternative example with similar elements to the medical system 10 shown by 100 added to the reference numbers, medical system 110 includes insertion device 112 and medical device 160. Insertion device 112 may include a handle 116 and a delivery shaft 118 similar to that of insertion device 12, and further include a clip 162 coupled to or integrally formed with handle 116.

Medical device 160 may be positioned in clip 162 and through handle 116 and delivery shaft 118 of insertion device 112. Clip 162 may fully encircle medical device 160, or may comprise an incomplete circular projection with a gap (not shown) such that thinner distal portions of medical device 160 may radially fit through the gap during insertion into handle 116, but that when in an assembled configuration, medical device 160 is radially secured by clip 162. Medical device 160 may be similar to medical device 14 and include a knob 162 with one or more protrusions 164, a plunger 122, a cap 124, an elongate member 126 with an end effector 132, and a spring 128 within a spring housing 130 (shown in cross-section).

As shown in FIG. 4, insertion device 112 may include a deflection lever 144 on handle 116, and clip 162 for medical device 160 is on the same side of insertion device 112 as deflection lever 144. As with insertion device 12, a proximal portion 138 of handle 116 may have a shape wider than intermediate portion 137 to provide a form-fitting shape to be ergonomically held by a user's hand. Then, deflection lever 144 may be positioned just proximal to clip 162 on a rounded corner portion of the proximal portion 138 such that, when held by a user, a user's thumb may manipulate deflection lever 144. Deflection lever 144 may be positioned on proximal portion 138 such that medical device 160 or clip 162 does not interfere with the full movement of the deflection lever 144.

Handle 116 also may include a hub 168 that is connected via a lumen through handle 116 and delivery shaft 118 to a distal end 140 with at least one distal opening 142 of delivery shaft 118. Hub 168 may be similar to hub 46, but is located at a distal position of the handle 116 on the same side of handle 116 as deflection lever 144 and may extend generally parallel to the body of handle 116. Medical device 160 may be introduced to handle 116 through hub 168, and elongate member 126 may extend from distal opening 142 in distal end 140 of delivery shaft 118. Insertion device 112 may also include a port 148 similar to port 48 discussed above.

Knob 164 of medical device 160 may be connected to plunger 122 to push and/or rotate plunger 122. Plunger 122 may pass axially through spring 128 and spring housing 130 and may be connected to elongate member 126. Cap 124 may have an axial lumen such that, when pressure is applied to knob 164, plunger 122 may slide through cap 124 and push elongate member 128 distally. Cap 124 may also include a seal around plunger 122. Elongate member 126 may be at least partially surrounded by a sheath 134, and sheath 134 may be coupled to an interior portion of cap 124. However, as discussed above with respect to elongate member 26, elongate member 126 may be employed without a sheath 134.

Hub 168 and cap 124 may be threaded such that cap 124 may be screwed onto hub 168 to couple medical device 160 to insertion device 112. Alternatively, hub 168 may be a female luer, and cap 124 may be a male luer, such that cap 124 may be joined to hub 168. Joining cap 124 to hub 168 may align elongate member 126, with or without sheath 134, to be flush with, slightly recessed within, or extended from the distal opening 142 of delivery shaft 118. Medical device 160 may further include an additional seal (not shown) and/or a sheath flush indicator marker (not shown) positioned distally to cap 124 to selectively position medical device 160 in the lumen connecting hub 168 to allow selective positioning of elongate member 126 when used with sheath 134 as discussed above regarding FIG. 2.

In one example similar to that shown in FIG. 3, elongate member 126 may be employed without a surrounding sheath. Here, elongate member 126 may have a length such that with cap 124 fully mounted on hub 168 and without action on plunger 122, elongate member 126 is flush with or slightly recessed in the distal opening 142 in distal end 140 of delivery shaft 118 of insertion device 112. Then, action on plunger 122 through knob 164 pushes elongate member 126 distally out of delivery shaft 118. If elongate member 126 has a self-expanding basket as end effector 132, the expandable basket expands as it extends out from the delivery shaft 118. A user may also rotate the extended elongate member 126 and end effector 132 by rotating knob 164. For example, a user may rotate end effector 132 to aid in expanding an expandable basket, in capturing a stone or material, or in repositioning or releasing a captured stone or material. Spring 128 serves to provide a biasing force to return knob 164 and plunger 122 once the force is removed, returning the elongate member 126 and end effector 132 to its initial position within the delivery shaft 118. The aforementioned steps may be repeated if the retrieval was unsuccessful. If successful, medical device 160 may be removed from insertion device 112 with the retrieved material captured and enclosed by the elongate member 126, or medical device 160 may be removed from a subject with removal of the insertion device 112.

In another example similar to that shown in FIG. 2, elongate member 126 may be employed with sheath 134. Here, elongate member 126 and sheath 134 may have a length such that with cap 124 fully mounted on hub 168 and without action on plunger 122, elongate member 126 and sheath 134 are flush with or extend slightly distal to the distal opening 142 in distal end 140 of delivery shaft 118. Then, action on plunger 122 through knob 164 pushes elongate member 126 distally out of sheath 134. If elongate member 126 has an expandable basket as end effector 132, the expandable basket may expand as it extends from the sheath 134. For example, a user may rotate end effector 132 to aid in expanding an expandable basket, in capturing a stone or material, or in repositioning or releasing a captured stone or material. Spring 128 serves to provide a biasing force to return knob 164 and plunger 122 once the force is removed, returning the elongate member 126 to its initial position within the sheath 134. The aforementioned steps may be repeated if the retrieval was unsuccessful. If successful, medical device 160 may be removed from insertion device 112 with the retrieved material captured and enclosed by the elongate member 126 and sheath 134, or medical device 160 may be removed from a subject with insertion device 112.

The foregoing examples allow a user to extend and rotate elongate member 126 with end effector 132 from distal opening 142 in distal end 140 of delivery shaft 118 with the user's thumb acting on knob 164. Concurrently or sequentially, the user may deflect the distal end 140 of delivery shaft 118 with the user's index finger acting on deflection lever 144, with the remaining fingers holding handle 116 on an opposing side. If the two maneuvers are performed concurrently, end effector 132 may be held in an extended position with a user's thumb while the user controls and/or deflects the distal end 140 of delivery shaft 118 with the user's index finger. Alternatively, a user may perform the maneuvers sequentially, using his or her thumb to separately control both knob 164 and deflection lever 144 The medical system 100 of this disclosure also allows the user to use his or her other hand to control and/or adjust the distal insertion and proximal retraction of delivery shaft 118 insertion device 112.

Figure 5:
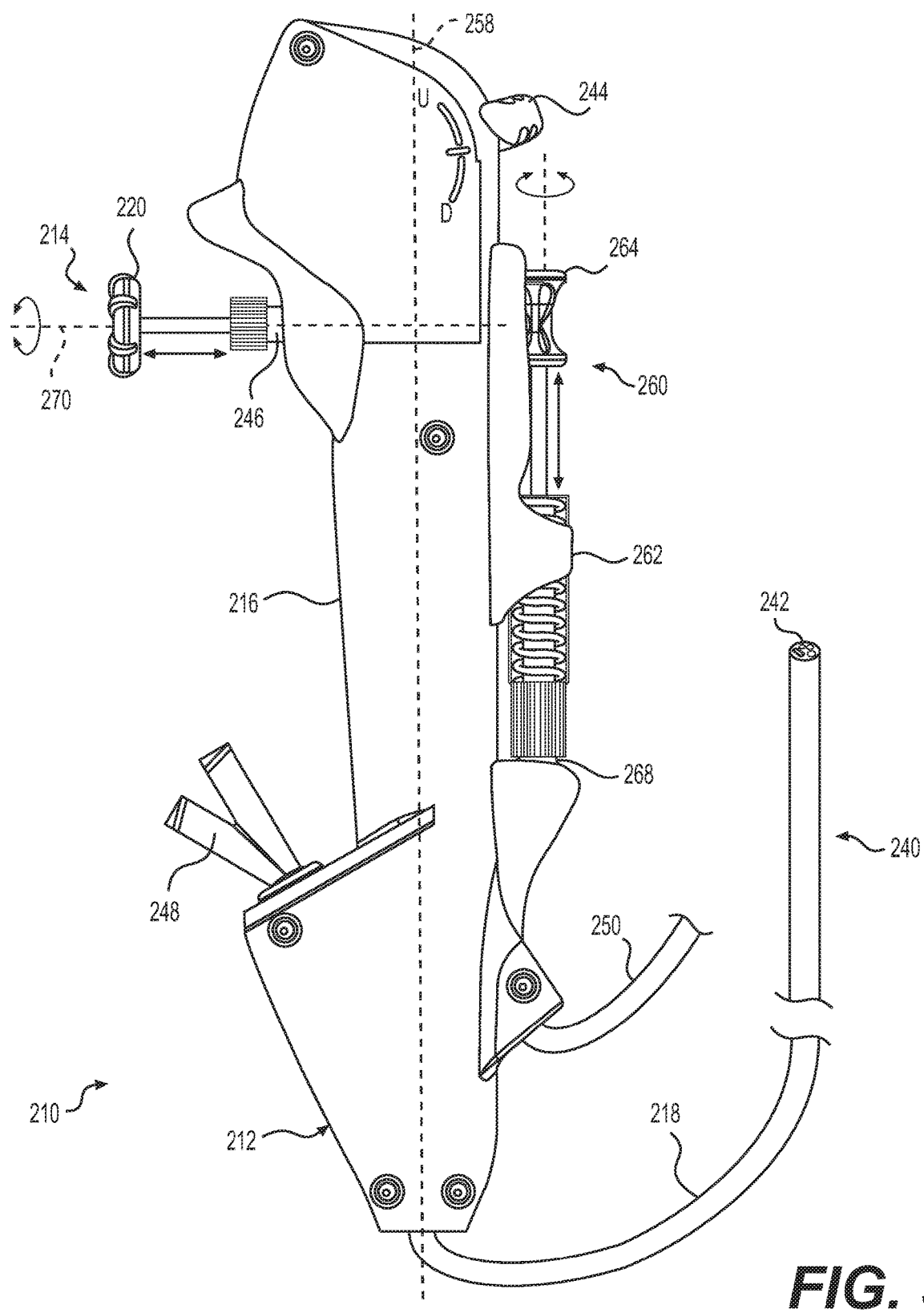
FIG. 5 illustrates an additional exemplary medical device, according to aspects of this disclosure.

As illustrated in FIG. 5, which is an alternative example with similar elements to the medical system 10 shown by 200 added to the reference numbers and similar elements to the medical system 110 shown by 100 added to the reference numbers, a medical system 210 includes an insertion device 212 and two medical device 214 and 260. Handle 216 of insertion device 212 may include a clip 262 and two hubs 246 and 268, such that medical devices 214 and 260 may be coupled to handle 216 in similar manners as shown and discussed with respect to FIGS. 1-4. Handle 216 may have a wider proximal portion and be similarly shaped as discussed regarding FIGS. 1-4.

Handle 216 may include four lumens connecting hubs 246 and 268, along with Y-connector port 248, to a distal opening 242 in a distal end 240 of delivery shaft 218. Alternatively, handle 216 may contain an internal splitter such that lumens from hubs 246 and 268 form one lumen extending through delivery shaft 218.

Medical system 210 may be used to deflect distal end 240 of delivery shaft 218 through deflection lever 244. Additionally, medical device 214 and 260 may be selectively extendable and rotatable through action on knobs 214 and 264. A user may concurrently or sequentially deflect, extend, and rotate the aforementioned elements with his or her thumb and index finger of one hand. A user may hold handle 216 such that the user's index finger is positioned to manipulate knob 220 and the user's thumb is positioned to manipulate knob 264. In this aspect, the user's thumb may also manipulate deflection lever 244. The user may also use his or her other hand to control and/or adjust the distal insertion and proximal retraction of delivery shaft 218 of insertion device 212. As shown in FIG. 5, longitudinal axis 270 of medical device 214 may extend normal to longitudinal axis 258 of medical device 260, and longitudinal axis 270 of medical device 214 may extend through knob 264 in at least the retracted position shown in FIG. 5.

Insertion of elongate members into insertion devices may include using an introducer sheath to rapidly introduce the elongate members of retrieval devices into the hubs. Additionally, it is contemplated that the configurations of the springs and the plungers may be effectively reversed such that actuation of the plungers serves to pull back sheaths distally, exposing end effectors. Moreover, it is also contemplated that the plunger need not have a circular cross-section and may be, for example, rectangular, triangular, hexagonal, or the like, in a situation where rotation of the end effectors of elongate members is not desired. Similarly, the cross-sectional geometry over the length of the plunger may vary in order to control the knob's rotational degree of freedom in various positions.

The insertion device and retrieval device may be manufactured separately and may be assembled before or during use, or may be manufactured together and/or integrally formed. Similarly, the shapes of the insertion device and retrieval device may vary from those shown in FIGS. 1-5 without departing from the scope of this disclosure, including, for example, a T-connector instead of the shown Y-connector or a differently shaped handle.

The disclosed medical device may enable quick positioning and deflection of an insertion device and extension of an elongate member with an end effector by a single user. The user may use only one hand to control deflection of the insertion device and the extension of the elongate member. The user may use his or her other hand to control and/or adjust the distal insertion or proximal retraction of the delivery shaft of the insertion device. As such, a single user may capture and remove a stone or material from inside a subject, reducing the time and number of people necessary for a procedure. Furthermore, the disclosed medical devices allows a user to provide torque while extending or retracting an end effector of an elongate member in a retrieval device.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

I claim:

1. A medical insertion device, comprising:
   a handle including a proximal portion, an intermediate portion, and a distal portion;
   a delivery shaft coupled to a distal most end of the distal portion of the handle;
   the handle further including
     a deflection lever, and
     a hub for introduction of a medical device, the hub and the deflection lever both being located in the proximal portion of the handle; and
   a medical device having an end effector at a distal end of an elongate member, and a knob at a proximal end of the elongate member operable to extend and/or rotate the end effector,
   wherein the medical device is coupled to the handle and through the delivery shaft via the hub,
   wherein axial action on the knob causes a plunger to push the elongate member distally,
   wherein rotational action on the knob causes the plunger to rotate the elongate member, and
   wherein the medical device is coupled to the hub via a cap of the medical device, and the plunger extends from the handle normal to an interface of the cap and the hub.

2. The medical insertion device of claim 1, wherein the deflection lever is positioned on a rounded proximal corner of the handle of the medical insertion device.

3. The medical insertion device of claim 1, wherein the deflection lever deflects a distal end of the delivery shaft through rotational movement of the deflection lever around a rounded proximal corner.

4. The medical insertion device of claim 3, wherein the hub is located on an opposite side of the proximal portion of the handle from the deflection lever.

5. The medical insertion device of claim 4, wherein, when the deflection lever is at a distal most position, the deflection lever is substantially parallel to the hub.

6. The medical insertion device of claim 4, wherein, when the deflection lever is at a proximal most position, the deflection lever forms an acute angle relative to a longitudinal axis of the hub.

7. The medical insertion device of claim 4, wherein the hub is distal to the deflection lever in the proximal portion of the handle.

8. The medical insertion device of claim 1, wherein the hub extends normal to a longitudinal axis of the handle.

9. The medical insertion device of claim 1, wherein the proximal portion of the handle is wider than the intermediate portion of the handle.

10. The medical insertion device of claim 1, wherein the hub is located in a recessed portion of the proximal portion of the handle.

11. The medical insertion device of claim 1, wherein the handle further includes a medical device clip extending on a same side of the handle as the deflection lever.

12. The medical insertion device of claim 1, wherein the axial movement of the plunger is biased by a spring surrounded by a spring housing; and wherein the spring housing is at least partially surrounded by at least one of a seal or a flush indicator.

13. A medical system, comprising a medical insertion device including a handle having a proximal portion, an intermediate portion, and a distal portion, and a delivery shaft, where the handle has a deflection lever in the proximal portion of the handle;

a medical device having an end effector at a distal end of an elongate member and a knob operable to extend and/or rotate the end effector;

wherein the medical device is coupled to the insertion device through a hub to a distal end of the delivery shaft, and where a portion of the medical device includes at least a portion located within the proximal portion of the handle when the medical device is coupled to the handle, wherein axial action on the knob causes a plunger to push the elongate member distally out of the distal end of the delivery shaft, and wherein rotational action on the knob causes the plunger to rotate the elongate member, and wherein the medical device is coupled to the hub via a cap of the medical device, and the plunger extends from the handle normal to an interface of the cap and the hub.

14. The medical system of claim 13, wherein the medical device is coupled to the hub via a cap; and wherein the axial movement of the plunger is biased by a spring.

15. The medical system of claim 14, wherein the hub and the deflection lever are on opposite sides of the proximal portion of the handle; and wherein the plunger extends normal to the longitudinal axis of the handle.

16. The medical system of claim 14, wherein the hub and the deflection lever are on a same side of the proximal portion of the handle; and wherein the knob extends parallel to the longitudinal axis of the handle.

* * * * *